(12) United States Patent
Coticone et al.

(10) Patent No.: US 6,780,588 B2
(45) Date of Patent: Aug. 24, 2004

(54) METHODS FOR THE REDUCTION OF STUTTER IN MICROSATELLITE AMPLIFICATION

(75) Inventors: Sulekha Rao Coticone, Half Moon Bay, CA (US); Will Bloch, White Salmon, WA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/850,590

(22) Filed: May 7, 2001

(65) Prior Publication Data

US 2002/0187475 A1 Dec. 12, 2002

(51) Int. Cl.[7] .............................. C12Q 1/68; C12P 19/34; C07H 21/02; C07H 21/04
(52) U.S. Cl. .......................... 435/6; 435/91.1; 435/91.2; 435/92.21; 536/23.1; 536/24.3
(58) Field of Search ........................ 435/6, 91.1, 91.2; 536/23.1, 24.3

(56) References Cited

U.S. PATENT DOCUMENTS

| | | | |
|---|---|---|---|
| 5,364,759 A | 11/1994 | Caskey et al. ................. | 435/6 |
| 5,545,539 A | 8/1996 | Miller ....................... | 435/91.2 |
| 5,571,674 A | 11/1996 | Hoshina et al. | |
| 5,580,728 A | 12/1996 | Perlin ........................... | 435/6 |
| 5,606,045 A | 2/1997 | Dandliker et al. | |
| 5,846,716 A | 12/1998 | Miller ........................... | 435/6 |
| 5,935,787 A | 8/1999 | Sidransky | |
| 6,077,664 A | 6/2000 | Slater et al. | |
| 6,156,512 A | 12/2000 | Schumm et al. ............... | 435/6 |
| 2001/0053518 A1 | 12/2001 | Ishiguro et al. | |

FOREIGN PATENT DOCUMENTS

| | | |
|---|---|---|
| DE | 44 11 588 C1 | 9/1995 |
| WO | WO 92/08800 * | 5/1992 |
| WO | WO 99/46400 | 9/1999 |

OTHER PUBLICATIONS

Saha et al, "A highly polymorphic microsatellite in the class II Eb gene allows tracing of major histocompatibility complex evolution in mouse", Proc. Natl. Acad. Sci. (1993) 90:5312–5316.*
Comings et al, "Sequence of human tryptophan 2, 3 Diooxygenase (TDO2) : Presence of a glucocorticoid response like element composed of GTT repeat and an intronic CCCCT repeat", Genomics (1995) 29:390–396.*
Atha, D.H. et al., "Detection of p53 point mutations by single strand conformation polymorphism : Analysis by capillary electrophoresis", Electrophoresis, 1998, 19, pp 172–179.
Baskaran, N. et al., "Uniform amplification of a mixture of deoxyribonucleic acids with varying GC content", Genome Research, 1996, 6, pp 633–638.
Bradshaw, PS. et al., "Fluroscent Bat–25 and BAT–26 analysis of T cell prolymphocytic leukaemia", BTS Leukemia, 1999, 13, pp 2104–2106.

Bruford et al.,"Microsatellites and their application to population genetic studies" Curr Biol, 1993, 3, 939–943.
Bruland O et al., Accurate determination of the number of CAG repeats in the Huntington disease gene using a sequence–specific internal DNA standard, Clin Genet, 1995, 55(3), 198–202.
Chen et al.,"Presence and instability of repetitive elements in sequences the altered expression of which characterizes risk for colonic cancer" Cancer Res.,1995, 55, 174–180.
Christensen M et al., "Comparasion of three methods of microsatellite detection", Scand J Clin Invest, 1999, 59 (3), 167–178.
Clark, J.M ."Novel non–templated nucleotide addition reactions catalyzed by procaryotic and eucaryotic DNA polymerases", Nucleic Acid Research, 1988, pp 9677–9686.
De La Chapelle,"Testing tumors for microsatellite instability" Eur J. Hum Genet., 1999, 7, 407–408.
Del Vecchio, P. et al., "The effects of polyols on the thermal stability of calf thymus DNA", Int'l Jrnl of Biol Macro, 1999, 24, pp 361–369.
Dimo–Simonin et al.,Forensic validation of the short tandem repaet HUMACTBP2 using capillary electrophoresis, Electrophoresis, 1998, 19(2), 256–61.
Edwards, a. et al., DNA typing and genetic mapping with trimeric and tetrameric tandem repeats', Am J. Hum. Genet, 1991, 49, pp 746–756.
Edwards, A. et al., "Genetic Variation at five trimeric and tetrameric tandem repeat loci in four human population groups", Genomics, 1992, 12, pp 241–253.
Eichler, E.E. et al.,"Length of uninterrupted CGG repeats determines instability in the FMRI1 gene" Nat Genet, 1994, 8, 88–94.
Eichler, E.E., et al., "Haplotype and interspersion analysis of the FMR1 CGG repeat identifies two different mutational pathways for the origin of the fragile X syndrome" Hum Mol Genet, 1996, 5, 319–330.
Frackman, S. et al., "Betaine and DMSO:Enhancing agents for PCR", Promega Notes 65, pp 27–29.
Frazier RR et al., "Validation of the applied biosystems Prism 377 automated sequencer for the forensic short tandem repeat analysis" Electrophoresis, 1996, 17(10), 1550–2.

(List continued on next page.)

Primary Examiner—Jeffrey Fredman
(74) Attorney, Agent, or Firm—Scott R. Bortner; Andrew K. Finn

(57) ABSTRACT

The invention provides a method for reducing stutter in the amplification of a microsatellite comprising the steps of providing a sample comprising a microsatellite having a G+C content of greater than 50%; contacting the sample with at least one enzyme having nucleic acid polymerase activity; and incubating the sample with the enzyme for a sufficient amount of time and under conditions sufficient to amplify the microsatellite; wherein the incubation is performed in the presence of an amount of sorbitol effective to reduce stutter relative to the amount of stutter observed in the absence of sorbitol. The invention also provides compositions containing sorbitol, kits for amplifying microsatellites having a G+C content of greater than 50%, and methods of using all of the foregoing.

77 Claims, 1 Drawing Sheet

OTHER PUBLICATIONS

Fre'geau et al.,"DNA typing with fluorescently tagged short tandem repeats: A sensitive and accurate approach to human identification" *Biotechniques*, 1993, 15, 100–119.

Fujigaski H et al., SCA12 is a rare locus for autosomal dominant cerebellar ataxia: a study of a n indian family,*Ann Neurol*, 2001, 49 (1), 117–21.

Goldstein et al.,"Genetic absolute dating based on microsatellites and the origin of modern humans" *Proc Natl Acad Sci USA*, 1995, 92, 6723–6727.

Hagelberg et al.,Identification of the skeletal remains of a murder victim by DNA analysis, *Nature*, 1991, 352, 427–429.

Hammond et al.,"Evaluation of 13 short tandem repeat loci for use in personal identification applications" *Am J Hum Genet*, 1994, 55, 175–189.

Hauge, X.Y. et al.,"A study of the origin of"shadow bands" seen when typing dinucleotide repeat polymorphisms by the PCR",*Human Molecular Genetics*, 1993, 2(4), pp 411–415.

Henke, W. et al., "Betaine improves the PCR amplification of GC–rich Dna Sequences" *Nucleic Acids Research*, 1997, 25(19), pp 3957–3958.

Hengen, P.N."Optimizing multiplex and LA–PCR with betaine", *TIBS*, 1997, pp 225–226.

Hite, J.M. et al., Factors affecting fidelity of DNA synthesis during PCR amplification of d(C–A)n d(G–T)n microsatellite repeats, *Nucleic Acids Research* 1996, 24(12), pp 2429–2434.

Ionov et al., "Ubiquitous somatic mutations in simple repeated sequences reveal a new mechanism for colonic carcinogenesis" *Nature*, 1993; 363, 558–561.

Khidiiatova IM et al., "[Expansion and mutation rate in CTG repeats in the myotonic dystrophy gene"]*Genetika*, 2000, 36(10), 1410–3.

Levinson, G. et al., "Slipped strand mispairing: A Major mechanism for DNA sequence evolution"*Mol. Biol.Evol*, 1987, 4(3), pp 203–221.

LeProust Em et al., Unexpected formation of parallel duplex in GAA and TTC trinucleotide repeates of Friedreich's ataxia', *J Mol Biol*, 2000, 302(5), 1063–80.

Lin, T.Y. et al., Why do some organisms use a urea–methylamine mixtures as osmolyte?*Biochemistry*, 1994, 33, pp 12695–12701.

Litt, M. et al. Shadow bands seen when typing polymorphic dinucleotide repeats:some causes and cures, *BioTechniques*, 1993, 15(2), pp 281–284.

Magnuson, V.L> et al., Substrate nucleotide determined non templated addition of adenine by taq DNA polymerase:implications for PCR–based genmotyping an cloning, *Biotechniques*, 1996, 21(4), pp 700–709.

Muller T et al., "GCG repeats and phenotype in oculopharyngeal muscular dystrophy", *Muscle Nerve*, 2001, 24(1), 120–2.

Murray, V. et al., "The determination of the sequences present in the shdow bands of a dinucleotide repeat PCR", *Nucleic Acids Research*, 1993, 21(10), pp 2395–2398.

Mytelka, D.S. et al., "Analysis and suppresion of DNA polymerase pauses associated with a trinucleotide consensus", *Nucleic Acids Research*, 1996, 24(14), pp 2774–2781.

Odelberg, S.J. et al., "A method for accurate amplification of polymorphic CA–repeat sequences", *PCR Methods and Applications*, 1993, pp 7–12.

Orosz, J.M. et al., "DNA melting temperatures and renaturation rates in concentrated alkylammonium salt solutions" *Biopolymers*, 1977, 16, pp 1183–1199.

Parsons et al.,"Microsatellite instability and mutations of the transforming growth factor b type ii receptor gene in colorectal cancer" *Cancer Res*, 1995, 55, 5548–5550.

Papp, A.C. et al., Strategies for amplifiction of trinucleotide repeats:Optimization of fragile X and androgen receptor PCR, *Molecular Diagnosis*, 1996,1(1), pp 59–64.

Primmer et al.,"Resolving genetic relationships with microsatellite markers: a parentage testing system for the swallow Hirundo rustica" *Mol Ecol.*, 1995, 4, 493–498.

Pyatt et al.,"Polymorphic variation at the BAT–25 and BAT–26 loci in individulas of african origin" *Am J. Pathol.*, 1999; 155, 349–353.

Rees, W.A. et al., "Betaine can eliminate the base pair composition dependence of DNA melting"*Biochemistry*, 1993, 32, pp 137–144.

Rouba A et al, "Patterns of allelic loss at the BRCA1 locus in Arabic women with breast cancer", *Int J Mol Med*, 2000, 6(5), 565–9.

Schweitzer, B. et al., "Immunoassays with rolling circle DNA amplification: A versatile platform for ultrasensitive antigen detection", *PNAS*, 2000, pp 10113–10119.

Stewart, I. "Symmetry and chaotic data", *Nature*, 1991, 354, pp 113.

Tahir MA et al., DNA typing of samples for polymarker, DQA1, and nine STR loci from a human body exhumed after 27 years, *J Forensic Sci*, 2000, 45 (4), 902–7.

Tautz, D., et al.,"Cryptic simplicity in DNA is a major source of genetic variation" *Nature*, 1986, 322(6080), 652–656.

Weber, J.L. "Informativeness of human (dC–dA)n (dG–dT)n polymorphisms" *Genomics*, 1990, 7, pp 524–530.

Weissensteiner T. et al., "Strategy for controlling preferential amplification and avoiding false negatives in PCR typing", *Biotechniques*, 1996, 21(6), pp 1100–1108.

Wenz, H. et al.,High precision genotyping by denaturing capillary electrophoresis *Genome Res.*, 1998, 8, 69–80.

Zhou et al.,"Allelicprofiles of mononucleotide repeat microsatellites in control individuals and in colorectal tumors with and without replication errors" *Oncogene*, 1997, 15, 1713–1718.

M. Miller et al., "Semiautomated Resolution of Overlapping Stutter Patterns in Genomic Microsatellite Analysis," Analytical Biochemistry, No. 251, 1997, pp. 50–56.

E. Chevet et al., "Low Concentration of Tetramethylammonium Chloride Increase Yield and Specificity of PCR," Nucleic Acids Research, vol. 23, No. 16, 1995, pp. 3343–3344.

Y. Sun et al., "PCR–direct Sequencing of GC–rich Region by Inclusion of 10% DMSO: Application to Mouse C–jun," BioTechniques, vol. 15, No. 3, 1993, pp. 372–374.

D. McDowell et al., "Localised Sequence Regions Possessing High Melting Temperatures Prevent the Amplification of DNA Mimic in Competitive PCR," Nucleic Acids Research, vol. 26, No. 14, 1998, pp. 3340–3347.

T. Notomi et al., "Loop–mediated Isothermal Amplification of DNA," Nucleic Acids Research, vol. 28, No. 12, 2000.

V. Potaman, "Prevention of Unexpectedly Long PCR Products Primed at Short Inverted Repeats," BioTechniques, vol. 27, No. 6, 1999, pp. 1110–1114.

Q. Liu et al., "Subcycling–PCR for Multiplex Long–Distance Amplification of Regions with High and Low GC Content:Application to the Inversion Hotspot in the Factor VIII Gene," BioTechniques, vol. 25, No. 6, 1998, pp. 1022–1028.

C. Rajendrakumar et al., "DNA Helix Destabilization by Proline and Betaine: Possible Role in the Salinity Tolerance Process," FEBS Letters, vol. 410, 1997, pp. 201–205.

H. Hamdan et al., "Automated Detection of Trinucleotide Repeats in Fragile X Syndrome," Molecular Diagnostics, vol. 2, No. 4, 1997, pp. 259–269.

M. Kovarova et al., "New Specificity and Yield Enhancer of Polymerase Chain Reactions," Nucleic Acids Research, vol. 28, No. 13, 2000, pp. e70.

* cited by examiner (TGCC)(TTCC)

METHODS FOR THE REDUCTION OF STUTTER IN MICROSATELLITE AMPLIFICATION

FIELD OF THE INVENTION

The invention relates to methods, compositions and kits for reducing stutter in polymerase chain reaction amplification of microsatellites. In certain embodiments, the invention relates to the use of sorbitol in polymerase chain reactions in an amount effective to reduce stutter in the amplification of mononucleotide, dinucleotide, trinucleotide, tetranucleotide and pentanucleotide microsatellites.

BACKGROUND OF THE RELATED ART

Microsatellites, or short tandem repeats (STRs), consist of tandemly repeated DNA sequence motifs of 1 to 6 nucleotides in length. They are widely dispersed and abundant in the eukaryotic genome, and are often highly polymorphic due to variation in the number of repeat units. This polymorphism renders microsatellites attractive DNA markers for genetic mapping, medical diagnostics and forensic investigation. The combination of PCR and gel or capillary electrophoresis under denaturing conditions has greatly improved the genotyping of microsatellite DNA sequences. However, PCR artifacts exhibited by non-proofreading enzymes and referred to as stutter and the terminal transferase side-reaction can complicate analysis of closely spaced microsatellite alleles.

Stutter signals differ from the PCR product representing the genomic allele by multiples of repeat unit size. For dinucleotide repeat loci, the prevalent stutter signal is generally two bases shorter than the genomic allele signal, with additional side-products that are 4 and 6 bases shorter. The multiple signal pattern observed for each allele especially complicates interpretation when two alleles from an individual are close in size (e.g., medical and genetic mapping applications) or when DNA samples contain mixtures from two or more individuals (e.g., forensic applications). Such confusion is maximal for mononucleotide microsatellite genotyping, when both genomic and stutter fragments experience one-nucleotide spacing.

There is a need in the art to develop PCR reaction conditions that minimize or eliminate stutter so that genetic analysis may be more accurate and reliable. This invention is directed to these, as well as other, important ends.

SUMMARY

In accordance with some embodiments of the methods of the invention, methods for reducing stutter in the amplification of a microsatellite are provided comprising the steps of:
  (a) providing a sample comprising a microsatellite of interest, in which the microsatellite has a G+C content of greater than 50%;
  (b) contacting the sample with at least one enzyme having nucleic acid polymerase activity; and
  (c) incubating the sample with the enzyme for a time and under conditions sufficient to amplify the microsatellite;
wherein said incubation is performed in the presence of an amount of sorbitol effective to reduce stutter relative to the amount of stutter observed in the absence of sorbitol.

The invention also provides methods for reducing stutter in the amplification of a mononucleotide microsatellite comprising the steps of:
  (a) providing a sample comprising a microsatellite of interest, in which the microsatellite has a G+C content of greater than 50%;
  (b) contacting the sample with at least one enzyme having nucleic acid polymerase activity; and
  (c) incubating the sample with the enzyme for a time and under conditions sufficient to amplify the microsatellite;
wherein the incubation is performed in the presence of an amount of sorbitol, wherein the sorbitol is effective to reduce stutter relative to the amount of stutter observed in the absence of sorbitol.

The invention also provides methods for reducing stutter in the amplification of a dinucleotide microsatellite comprising the steps of:
  (a) providing a sample comprising a microsatellite of interest, in which the microsatellite has a G+C content of greater than 50%;
  (b) contacting the sample with at least one enzyme having nucleic acid polymerase activity; and
  (c) incubating the sample with the enzyme for a time and under conditions sufficient to amplify the microsatellite; wherein the incubation is performed in the presence of an amount of sorbitol effective to reduce stutter relative to the amount of stutter observed in the absence of sorbitol.

The invention further provides methods for reducing stutter in the amplification of a trinucleotide microsatellite comprising the steps of:
  (a) providing a sample comprising a microsatellite of interest, in which the microsatellite has a G+C content of greater than 50%;
  (b) contacting the sample with at least one enzyme having nucleic acid polymerase activity; and
  (c) incubating the sample with the enzyme for a time and under conditions sufficient to amplify the microsatellite; wherein the incubation is performed in the presence of an amount of sorbitol effective to reduce stutter relative to the amount of stutter observed in the absence of sorbitol.

The invention further provides methods for reducing stutter in the amplification of a tetranucleotide microsatellite comprising the steps of:
  (a) providing a sample comprising a microsatellite of interest, in which the microsatellite has a G+C content of greater than 50%;
  (b) contacting the sample with at least one enzyme having nucleic acid polymerase activity; and
  (c) incubating the sample with the enzyme for a time and under conditions sufficient to amplify the microsatellite; wherein the incubation is performed in the presence of an amount of sorbitol effective to reduce stutter relative to the amount of stutter observed in the absence of sorbitol.

The invention further provides methods for reducing stutter in the amplification of a pentanucleotide microsatellite comprising the steps of:
  (a) providing a sample comprising a microsatellite of interest, in which the microsatellite has a G+C content of greater than 50%;
  (b) contacting the sample with at least one enzyme having nucleic acid polymerase activity; and
  (c) incubating the sample with the enzyme for a time and under conditions sufficient to amplify the microsatellite; wherein the incubation is performed in the presence of an amount of sorbitol effective to reduce stutter relative to the amount of stutter observed in the absence of sorbitol.

In further embodiments of the methods of the invention, methods are provided comprising the steps of:

(a) providing a sample comprising a nucleic acid that contains one or more microsatellites selected from the group consisting of mononucleotide microsatellites, dinucleotide microsatellites, trinucleotide microsatellites, tetranucleotide microsatellites and pentanucleotide microsatellites; and (b) amplifying at least one nucleobase sequence of said nucleic acid, said nucleobase sequence comprising at least one of said microsatellites; said amplified microsatellite having a G+C content of greater than 50%; wherein said amplification is performed in the presence of sorbitol.

Also provided in accordance with the present invention are methods for performing polymerase chain reaction amplification of a microsatellite selected from the group consisting of mononucleotide microsatellites, dinucleotide microsatellites, trinucleotide microsatellites, tetranucleotide microsatellites and pentanucleotide microsatellites, said microsatellite having a G+C content of greater than 50%; said method comprising the step of contacting said microsatellite with a polymerase in the presence of an amount of sorbitol effective to reduce the amount of stutter arising from said amplification relative to the amount of such stutter observed in the absence of sorbitol.

Also provided by the present invention are methods of detecting cancer or a pre-cancerous condition and genetic disorders, in a subject comprising amplifying a region of DNA from a subject, wherein said region comprises a microsatellite selected from the group consisting of a mononucleotide repeat, a dinucleotide repeat, a trinucleotide repeat, a tetranucleotide repeat and a pentanucleotide repeat, wherein said amplification comprises the steps of:

(a) providing a sample comprising a nucleic acid that contains a nucleic acid having a microsatellite instability, (b) amplifying at least one nucleobase sequence of the nucleic acid, in which the nucleobase sequence comprises at least one of the microsatellites; and (c) detecting alterations of the microsatellite as compared to corresponding microsatellites amplified from control tissue; the amplified microsatellite having a G+C content of greater than 50%; wherein the amplification is performed in the presence of a sufficient amount of sorbitol effective to reduce stutter from that observed in the absence of sorbitol.

In some embodiments, the cancer or cancerous condition is chronic lymphocytic leukemia. In further embodiments, the microsatellite amplification comprises at least one genetic locus, for example, CAG/CTG, CCG/CGG, and CGA/TCG.

In some embodiments, the genetic disorder is Huntington's disease or a spinocerebellar ataxia. In further embodiments, the microsatellite amplification comprises at least one genetic locus, for example, CAG/CTG.

In other embodiments, the disorder is a psychiatric disorder. In further embodiments, the microsatellite amplification comprises at least one genetic locus, for example, CCCCT/AGGGG.

In some embodiments, the present invention also provides methods of genetic mapping comprising amplifying a plurality of regions of DNA from a sample containing DNA from a subject, wherein the regions comprise at least one microsatellite selected from the group consisting of a mononucleotide repeat, a dinucleotide repeat, a trinucleotide repeat, a tetranucleotide repeat and a pentanucleotide repeat, wherein the amplification comprises the steps of:

(a) contacting said DNA with a enzyme at least one enzyme having nucleic acid polymerase activity; and (b) incubating said sample with the enzyme for a time and under conditions sufficient to amplify the regions; and (c) separating amplified regions, forming a microsatellite pattern; wherein the incubation is performed in the presence of an amount of sorbitol effective to reduce stutter relative to the amount of stutter observed in the absence of sorbitol.

In further embodiments, the present invention also provides methods of personal genetic identification comprising amplifying a plurality of regions of DNA from a sample containing DNA from a subject, wherein said regions comprise at least one microsatellite selected from the group consisting of a mononucleotide repeat, a dinucleotide repeat, a trinucleotide repeat, a tetranucleotide repeat and a pentanucleotide repeat; wherein the microsatellite has a G+C content of greater than 50%; wherein the amplification comprises the steps of:

(a) contacting said DNA with a enzyme at least one enzyme having nucleic acid polymerase activity; and (b) incubating the sample with the enzyme for a time and under conditions sufficient to amplify the regions;

(c) separating amplified regions, forming a microsatellite pattern; and (d) comparing the microsatellite pattern with a corresponding microsatellite pattern derived from the a DNA sample from a second source; wherein the incubation is performed in the presence of an amount of sorbitol effective to reduce stutter relative to the amount of stutter observed in the absence of sorbitol.

In some embodiments, the subject is a forensic sample and a said second source comprises at least one selected from the group consisting of the presumed matching source, a family member of the presumed matching source, and a database of sources.

In some embodiments of the methods of the invention, where the microsatellite is a dinucleotide microsatellite, the microsatellite comprises a dinucleotide repeat is CG/CG. In further embodiments where the microsatellite is a trinucleotide microsatellite, the microsatellite comprises a trinucleotide repeat selected from the group consisting of CAG/CTG, CCG/CGG, and CGA/TCG. In further embodiments where the microsatellite is a tetranucleotide microsatellite, the microsatellite comprises a tetranucleotide repeat consisting of TGCC/GGCA. In further embodiments where the microsatellite is a pentanucleotide microsatellite, the microsatellite comprises a pentanucleotide repeat consisting of CCCCT/AGGGG.

In some embodiments of the method of the invention, the microsatellite has a G+C content of greater than 50%. In further embodiments, the microsatellite has a G+C content of greater than 66%. In further embodiments, the microsatellite has a G+C content of 75% or more. In further embodiments, the microsatellite has a G+C content of 100%.

In some embodiments of the invention, the amount of stutter is reduced to 90% or less than the amount of stutter obtained in the absence of sorbitol. In other embodiments the amount of stutter is reduced to 80% or less. In other embodiments, the amount of stutter is reduced to 70% or less. In other embodiments, the amount of stutter is reduced to 60% or less. In other embodiments, the amount of stutter is reduced to 50% or less. In other embodiments, the amount of stutter is reduced to 40% or less. In other embodiments, the amount of stutter is reduced to 30% or less.

In some embodiments of the methods of the invention, the amplification comprises contacting said nucleobase sequence with an enzyme having a polymerase activity. For example, the enzyme having polymerase activity may be selected from the group consisting of a DNA polymerase from *Thermus aquaticus, Thermus thermophilus*, other Thermus species, Bacillus species, Thermococcus species, Thermotoga species, and Pyrococcus species. For example, suitable polymerases include AmpliTaq Gold® DNA polymerase; AmpliTaq® DNA Polymerase; AmpliTaq® DNA Polymerase, Stoffel fragment; rTth DNA Polymerase; rTth DNA Polymerase XL; Bst DNA polymerase large fragment from *Bacillus stearothermophilus;* Vent and Vent Exo- from *Thermococcus litoralis;* Tma from *Thermotoga maritima;* Deep Vent and Deep Vent Exo- and Pfu from Pyrococcus; and mutants, variants and derivatives thereof.

Also provided in certain embodiments of the invention are compositions comprising:
(a) a nucleic acid sequence comprising a microsatellite, in which the microsatellite has a G+C content of greater than 50%, the microsatellite being selected from the group consisting of mononucleotide microsatellites, dinucleotide microsatellites, trinucleotide microsatellites, tetranucleotide microsatellites and pentanucleotide microsatellites;
(b) at least two primers, each of said primers having a sequence that is substantially complementary to a portion of the nucleic acid sequence that is adjacent to the microsatellite;
(c) at least one enzyme having nucleic acid polymerase activity; and (d) sorbitol.

In some embodiments of the methods and compositions of the invention, sorbitol is present in an amount of from 1.5 to 3.5 M. In other embodiments, sorbitol is present in an amount of 2.0 to 3.0 M. In other embodiments, sorbitol is present in an amount of 2.0 M.

In some embodiments of the invention, at least 0.5 mM each of dNTPs are used. In other embodiments, at least 1 mM dNTPs are used.

In some embodiments, the present invention also provides kits for amplification of a target nucleic acid sequence, the target nucleic acid sequence comprising a microsatellite having a G+C content of greater than 50%, selected from the group consisting of mononucleotide microsatellites, dinucleotide microsatellites, trinucleotide microsatellites, tetranucleotide microsatellites, and pentanucleotide microsatellites comprising, in separate containers: a polymerase, a plurality of deoxynucleotide triphosphates; and sorbitol. In some embodiments of the compositions and kits of the invention, the polymerase is selected from the group consisting of a DNA polymerase from *Thermus aquaticus, Thermus thermophilus*, other Thermus species, Bacillus species, Thermococcus species, Thermotoga species, and Pyrococcus species. For example, suitable polymerases include, but are not limited to, AmpliTaq Gold® DNA polymerase; AmpliTaq® DNA Polymerase; AmpliTaq® DNA Polymerase, Stoffel fragment; rTth DNA Polymerase; rTth DNA Polymerase XL; Bst DNA polymerase large fragment from *Bacillus stearothermophilus;* Vent and Vent Exo- from *Thermococcus litoralis;* Tma from *Thermotoga maritima;* Deep Vent and Deep Vent Exo- and Pfu from Pyrococcus; and mutants, variants and derivatives thereof.

In some further embodiments of the invention, methods are provided in which a sample containing nucleic acid that is suspected of containing one or more microsatellites having a G+C content of greater than 50% is contacted with an enzyme that polymerizes nucleotides in the presence of an effective amount of sorbitol to reduce observed stutter relative to the amount of stutter observed in the absence of sorbitol, and amplifying at least one nucleobase sequence containing at least one microsatellite of the nucleic acid contained in the sample. Such microsatellites may include mononucleotide, dinucleotide, trinucleotide, tetranucleotide microsatellites and/or pentanucleotide microsatellites.

DETAILED DESCRIPTION

Figure 1:
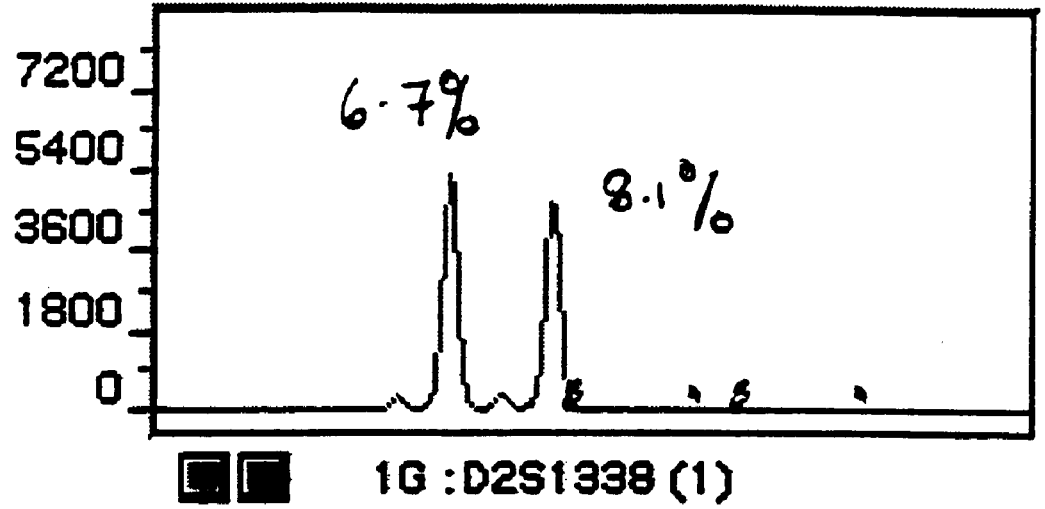
FIG. 1 shows GeneScan traces from PCR amplifications of a tetranucleotide microsatellite $((CTTT/AAAG)_n)$ for control conditions (upper panel) and with added sorbitol (lower panel).
Figure 1:
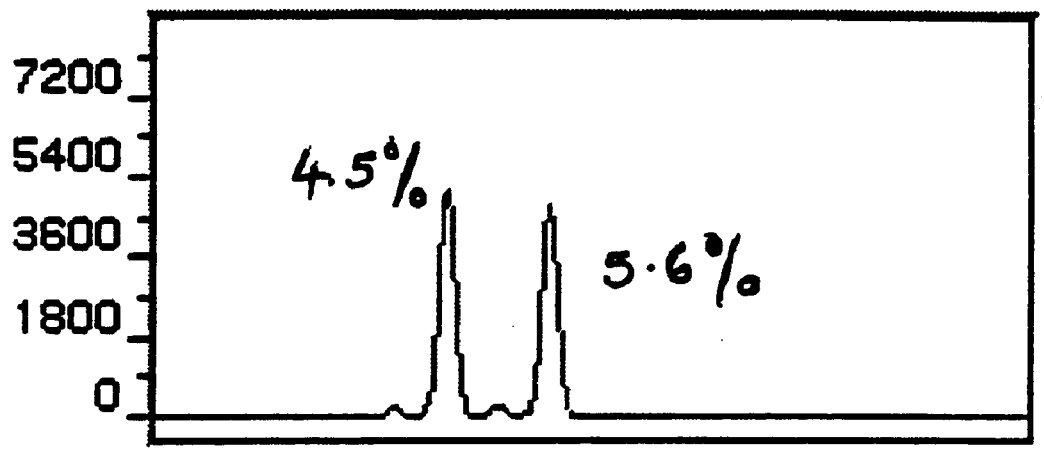

Most of the words used in this specification have the meaning that would be attributed to those words by one skilled in the art. Words specifically defined in the Specification have the meaning provided in the context of the present invention as a whole, and as are typically understood by those skilled in the art. In the event that a conflict arises between an art-understood definition of a word or phrase and a definition of the word or phrase as specifically taught in this specification, the specification shall control. Headings used herein are merely for convenience, and are not to be construed as limiting in any way.

Standard reference works setting forth the general principles of recombinant DNA technology known to those of skill in the art include Ausubel et al., CURRENT PROTOCOLS IN MOLECULAR BIOLOGY, John Wiley & Sons, New York, 1998 Molecular Cloning: A Laboratory Manual (3rd ed.) Sambrook, J. & D. Russell, Eds.Cold Spring Harbor Laboratory Press, Cold Spring Harbor, N.Y. (2001); Kaufman et al., Eds., HANDBOOK OF MOLECULAR AND CELLULAR METHODS IN BIOLOGY AND MEDICINE, CRC Press, Boca Raton, 1995; McPherson, Ed., DIRECTED MUTAGENESIS: A PRACTICAL APPROACH, IRL Press, Oxford, 1991.

As used herein, the term "microsatellite" refers to a genetic locus comprising a short (e.g., 1–5 nucleotide), tandemly repeated sequence motif. As used herein "mononucleotide microsatellite" refers to a genetic locus comprising a repeated nucleotide (e.g., C/G). "Dinucleotide microsatellite" refers to genetic locus comprising a motif of two nucleotides that is tandemly repeated (e.g., GC/GC). "Trinucleotide microsatellite" refers to a genetic locus comprising a motif of three nucleotides that is tandemly repeated (e.g., CAG/CTG, CGA/TCG, CGG/CCG). "Tetranucleotide microsatellite" refers to a genetic locus comprising a motif of four nucleotides that is tandemly repeated (e.g., TGCC/GGCA). "Pentanucleotide microsatellite" refers to a genetic locus comprising a motif of five nucleotides that is tandemly repeated (e.g., CCCCT/AGGGG). Microsatellites may contain repeat-motif interspersions, or "cryptically simple sequence" (Tautz, D. et al. (1986) *Nature* 322(6080): 652–656). Such repeat-motif interspersions include simple repeat-motif interspersions wherein the microsatellite contains one or more interspersed repeats with the same length as the tandemly repeated sequence motif, but a different repeat sequence (Eichler, E. E. et al. (1994) *Nat. Genet.* 8:88–94; Eichler, E. E. et al. (1996) *Hum. Mol. Genet.* 5:319–330). For example, if the tandemly repeated sequence motif is TGCC, a simple repeat-motif interspesion may appear as follows: TGCC(TCTG)₂(TGCC)₃, wherein the interspersed repeat "TCTG" interrupts the repeat of the TGCC tandemly repeated sequence motif. Repeat-motif interspersions also include more complex repeat-motif interspersions wherein the repeat motif interspersion is not the same length as the tandemly repeated sequence motif. For example, if the tandemly repeated sequence motif is TGCC, a complex repeat-motif interspersion may appear as follows: (TGCC)₃TG(TGCC)₃TGC(TGCC)₂, wherein the tandemly repeated sequence motif is interrupted by TG and TGC. Other more complex repeat motif interspersions include the combination of the simple repeat-motif interspersion and the complex repeat-motif interspersion in the same microsatellite. For example, such a complex sequence repeat-motif interspersion may appear as follows: (TGCC)$_n$(TCTG)$_o$(TGCC)₃TG(TGCC)₃TGC(TGCC)₂ TGCCC(TGCC)$_p$, wherein both forms of interspersed repeats interrupt the tandemly repeated sequence motif, TGCC. Microsatellites with and without interspersed repeats are encompassed by the term "microsatellites" as used herein.

As used herein, the term "stutter" or "stutter signal" refers to a PCR artifact wherein microsatellites are incorrectly amplified such that a diverse population of fragments of varying length are produced for each allele in the genomic source DNA. A typical "stutter signal" results from one or more PCR products that differ from the appropriate length of the microsatellite-containing fragment by one or more repeat-unit lengths of the microsatellite. As used herein "appropriate length of the microsatellite-containing fragment" refers to the length predicted from the primer sequences and the genomic target sequence, with or without one added nucleotide, depending on whether the PCR conditions promote or suppress the polymerase terminal transferase side reaction. A stutter signal may be perceived with the naked eye, such as by examining a band on an agarose or polyacrylamide gel, or may be perceived with the aid of instrumentation. A stutter signal seen on a gel typically appears as a blurry, shadow band due to microsatellites which are incorrectly amplified such that a diverse population of fragments of varying length are produced. A stutter signal as detected on a GeneScan trace or other electropherogram may appear as a quantified signal, such as a peak on a graph. Stutter signals may be represented by any means, such as, but not limited to brightness, intensity (e.g., maximum intensity), magnitude of a signal output (e.g., peak height, integration of the area of a peak, peak width at half peak height), and the like. For example, in a GeneScan trace for a tetranucleotide microsatellite, a major stutter signal is typically seen as a peak found at four nucleobase units downfield (i.e., at a location corresponding to a shorter fragment) on the electropherogram from the major peak, which represents the allele. Other, less prominent stutter signals may be found at 8 and 12 nucleobase units downfield on the chromatogram. As used herein, the term "reducing stutter" is intended to mean the production of lower amounts of amplified stutter product, as reflected by a decrease in the number or signal intensity of stutter fragments.

As used herein "sorbitol" refers to the polyol (polyhydric alcohol) corresponding to glucose, represented by the following structural formula:

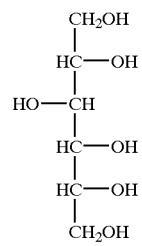

As used herein, the term "isolated nucleic acid molecule" refers to a nucleic acid molecule (DNA or RNA) that has been removed from its native environment.

As used herein, "DNA" refers to deoxyribonucleic acid in its various forms as understood in the art, such as genomic DNA, cDNA, isolated nucleic acid molecules, vector DNA, chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or of chemical precursors or other chemicals when chemically synthesized.

As used herein "nucleobase sequence" refers to a sequence of consecutive nucleobases.

As used herein, "anneal" refers to specific interaction between strands of nucleotides wherein the strands bind to one another substantially based on complementarity between the strands as determined by Watson-Crick base pairing. It is not necessary that complementarity be 100% for annealing to occur.

As used herein, "amplifying" refers to enzymatically increasing the amount of a specific nucleotide sequence in a polymerase chain reaction.

As used herein "incubating" refers to a maintaining a state of controlled conditions such as temperature over a period of time.

As used herein "denaturation" refers to the separation of nucleotide strands from an annealed state. Denaturation may be induced by a number of factors including ionic strength of the buffer, temperature, or chemicals that disrupt base pairing interactions.

As used herein "G+C content" refers to the relative amount of guanosine and cytosine present in a given nucleic acid or portion thereof that is of interest, such as a microsatellite. The "G+C content" of a given nucleobase sequence, expressed in percent, can be calculated from the formula 100(#G+#C)/Tot where #G is the number of guanine nucleobases in the nucleobase sequence, #C is the number of cytosine nucleobases in the nucleobase sequence, and Tot is the total number of nucleobases in the nucleobase sequence.

As used herein, "sufficient amount of time" when referring to time for the amplification of nucleic acid, refers to the time which allows the enzyme used to complete the polymerization of deoxynucleotide triphosphates into the amplifying nucleic acid. The amount of time required varies depending on several factors which are well-known by persons of ordinary skill in the art. General principles of PCR and strategies for amplification may be found in such texts as, for example, Ausubel et al., CURRENT PROTOCOLS IN MOLECULAR BIOLOGY, John Wiley & Sons, New York, 2001 and THE POLYMERASE CHAIN REACTION, Mullis, K. B., F. Ferre, and R. A. Gibbs, Eds., Birkhauser, Boston, 1994; AND MOLECULAR CLONING: A LABORATORY MANUAL (3rd ed.) Sambrook, J. & D. Russell, Eds. Cold Spring Harbor Laboratory Press, Cold Spring Harbor, N.Y. (2001).

As used herein "conditions sufficient to amplify microsatellites" refers to reaction conditions for the PCR reactions. The reaction conditions include the chemical components of the reaction and their concentrations, the temperatures used in the reaction cycles, the number of cycles of the reaction, and the durations of the stages of the reaction cycles.

Typically, buffered water is used as the solvent for the reaction. The other chemical components of standard PCR reactions include a DNA polymerase, deoxyribonucleoside triphosphates ("dNTPs"), oligonucleotide primers, divalent metal ion, and a DNA sample expected to contain the PCR target.

The solvent used for PCR typically contains a buffering agent such as Tris-HCl and non-buffering salts such as KCl. The buffering agent may be any known buffers in the art, and may be varied to optimize PCR results by routine experimentation. Persons of ordinary skill in the art will readily be able to determine optimal buffering conditions. Some PCR buffers may be optimized depending on the enzyme used. As an example, but not by way of limitation, AmpliTaq Gold® DNA polymerase has an optimum KCl concentration of 50 mM, AmpliTaq® DNA Polymerase, Stoffel fragment has an optimum KCl concentration of 10 mM, and rTth DNA Polymerase and rTth DNA Polymerase XL, have an optimum KCl concentration of 75–100 mM.

Divalent metal ions are often advantageous to allow the polymerase to function efficiently. For example, but not by way of limitation, magnesium ion allows certain DNA polymerases to function effectively. Typically, $MgCl_2$ or $MgSO_4$, is added to reaction buffers to supply the optimum magnesium ion concentration. The magnesium ion concentration required for optimal PCR amplification may depend on the specific set of primers and template used. Thus, the amount of magnesium salt added to achieve optimal amplification is often determined empirically, and is a routine practice in the art. Generally, the concentration of magnesium ion for optimal PCR can vary between 1 and 10 mM. A typical range of magnesium ion concentration in PCR reactions is between 1.0 and 4.0 mM, varying around a midpoint of 2.5 mM.

Deoxynucleotide triphosphates ("dNTPs"), which are the building blocks of the amplifying nucleic acid molecules, are typically supplied in standard PCR reactions at a concentration of 40–200 $\mu M$ each of deoxyadenosine triphosphate ("dATP"), deoxyguanosine triphosphate ("dGTP"), deoxycytidine triphosphate ("dCTP") and thymidine triphosphate ("dTTP"). Other dNTPs, such as deoxyuridine triphosphate ("dUTP"), and dNTP analogs, and conjugated dNTPs may also be used, and are encompassed by the term "dNTPs" as used herein. While use of dNTPs at such concentrations is amenable to the methods of the invention, concentrations of dNTPs higher than 200 $\mu M$ may be advantageous. Thus, in some embodiments of the methods of the invention, the concentration of each dNTP is generally at least 500 $\mu M$ and may range up to 2 mM. In some further embodiments, concentration of each dNTP may range from 0.5 mM to 1 mM.

The enzyme that polymerizes the nucleotide triphosphates into the amplified fragments of the PCR may be any DNA polymerase, including heat-resistant polymerases known in the art. Polymerases that may be used in the invention include, but are not limited to DNA polymerases from such organisms as *Thermus aquaticus, Thermus thermophilus, Thermococcus litoralis, Bacillus stearothermophilus, Thermotoga maritima* and Pyrococcus ssp. The enzyme may be isolated from the source bacteria, produced by recombinant DNA technology or purchased from commercial sources. For example, DNA polymerases are available from Applied Biosystems and include AmpliTaq Gold® DNA polymerase; AmpliTaq® DNA Polymerase; AmpliTaq® DNA Polymerase, Stoffel fragment; rTth DNA Polymerase; and rTth DNA Polymerase XL. Other suitable polymerases include, but are not limited to Tne, Bst DNA polymerase large fragment from *Bacillus stearothermophilus,* Vent and Vent Exo- from *Thermococcus litoralis,* Tma from *Thermotoga maritima,* Deep Vent and Deep Vent Exo- and Pfu from Pyrococcus, and mutants, variants and derivatives of the foregoing.

Oligonucleotide primers are added to the reaction and demarcate the 5' and 3' ends of the amplified fragment. One oligonucleotide primer anneals to the sense (+strand) of the denatured, template DNA, and the other oligonucleotide primer anneals to the antisense (−strand) of the denatured, template DNA. Typically, oligonucleotide primers are 12–25 nucleotides in length, however, they may be shorter or longer depending on the specific template sequence to be amplified, and the length of the primer is not essential to the operation of the invention. Oligonucleotide primers may be designed to anneal to specific portions of DNA that flank a microsatellite of interest to specifically amplify the portion of DNA between the primer-complementary sites. Generally, oligonucleotide primers are chemically synthesized. One of ordinary skill in the art may easily design specific primers to amplify a target microsatellite of interest. Furthermore, there are many known primer sequences to amplify microsatellite regions. Any of these may be used, and are within the scope of the invention.

The oligonucleotide primers may be composed of adenosine, thymidine, guanosine, cytidine, uracil, nucleoside analogs (e.g., locked nucleic acids (LNA), peptide nucleic acid (PNA), phosporamidites) and nucleosides containing or conjugated to chemical moieties such as radionuclides (e.g., $^{32}P$, $^{35}S$), fluorescent molecules, minor groove binders, or any other nucleoside conjugate known in the art.

In some embodiments of the invention, a fluorophore is used to tag at least one primer of the PCR reaction. In some embodiments primers for different target fragments can be tagged with different fluorophores (that produce differently colored products) and may be used in the same multiplex PCR reaction and subsequently analyzed together. Typically, the forward primer is tagged, but the reverse primer may also be tagged. Examples of fluorophores include, but are not limited to, fluorescein (which absorbs maximally at 492 nm and emits maximally at 520 nm); TAMRA, N,N,N',N'-tetramethyl-6-carboxyrhodamine (which absorbs maximally at 555 nm and emits maximally at 580 nm); FAM, 5-carboxyfluorescein (which absorbs maximally at 495 nm and emits maximally at 525 nm); JOE, 2',7'-dimethoxy-4', 5'-dichloro-6-carboxyfluorescein (which absorbs maximally at 525 nm and emits maximally at 555 nm), ROX, 6-carboxy-X-rhodamine (which absorbs maximally at 585 nm and emits maximally at 605 nm); CY3 (which absorbs maximally at 552 nm and emits maximally at 570 nm), CY5 (which absorbs maximally at 643 nm and emits maximally at 667 nm); TET, tetrachloro-fluorescein (which absorbs maximally at 521 nm and emits maximally at 536 nm); and HEX, hexachloro-fluorescein (which absorbs maximally at 535 nm and emits maximally at 556 nm).

Other known components of PCR reactions may be used within the scope of the invention. Such components include, but are not limited to, detergents (e.g., Triton X-100, Nonidet P-40 (NP-40), Tween-20) and agents that disrupt mismatching of nucleotide pairs, such as dimethylsulfoxide (DMSO), and tetramethylammonium chloride (TMAC).

PCR reaction times, temperatures and cycle numbers may be varied to optimize a particular reaction as a matter of routine experimentation. Those of ordinary skill in the art will recognize the following as guidance in determining the various parameters for PCR reactions, and also will recognize that variation of one or more conditions is within the scope of the invention.

PCR reaction temperature and time are determined in three stages: denaturation, annealing and extension. One round of denaturation, annealing and extension is referred to as a "cycle." Denaturation is generally conducted at a temperature that permits the strands of DNA to separate, yet not destroy polymerase activity. Generally, thermoresistant polymerases are used. However, heat-labile polymerases may be used if they are replenished after each denaturation step of the PCR. Thermoresistant polymerases can withstand high temperatures and maintain some level of activity. Typically, denaturation is conducted above 90° C. and below 100° C. In some embodiments, denaturation is conducted at a temperature of 94–95° C. Denaturation of DNA is generally conducted for at least 1 to 30 seconds. In some embodiments, denaturation is conducted for 1 to 15 seconds. In other embodiments, denaturation is conducted for up to 1 minute or more. In addition to the denaturation of DNA, for some polymerases, such as AmpliTaq Gold®, incubation at the denaturation temperature also serves to activate the enzyme. Therefore, it may be advantageous to allow the first step of PCR (denaturation) to be longer than subsequent denaturation steps when these enzymes are used.

During the annealing phase, oligonucleotide primers anneal to the target DNA in their regions of complementarity and are substantially extended by the DNA polymerase once the latter has bound to the primer-template duplex.

In a conventional PCR, the annealing temperature typically is at or below the melting point ($T_m$) of the least stable primer-template duplex, where $T_m$ can be estimated by any of several theoretical methods well known to practitioners of the art. For example, the $T_m$ may be determined by the formula:

$$T_m = (4° C. \times \text{number of G and C bases}) + (2° C. \times \text{number of A and T bases})$$

Typically, in standard PCRs, the annealing temperature is 5° C. to 10° C. below the estimated $T_m$ of the least stable primer-template duplex. The annealing time is between about 30 seconds and 2 minutes. However, in certain embodiments of the methods of the invention, the high concentration of sorbitol increases reagent viscosity and appears to slow certain steps of the reaction (e.g., primer annealing and polymerase binding to the primer-template duplex). Thus, in certain embodiments of the methods of the invention, the annealing step is performed for a longer period of time than would be used in standard PCR protocols, typically for at least 3 minutes and as long as 5 to 6 minutes.

Sorbitol not only increase reaction viscosity, but is also a mild DNA denaturant. Thus, in certain embodiments of the methods of the invention, it is may be advantageous to use a lower temperature for annealing primers to the template than would be used by one of ordinary skill in the art for standard PCR reactions. In general, temperatures lower than 10° C. below the $T_m$ (estimated in the absence of additive) may be employed in certain embodiments of the invention.

The annealing phase typically is followed by an extension phase. "Extension" is conducted for a sufficient amount of time to allow the enzyme to complete primer extension into the appropriately sized fragments. As discussed above, the addition of high concentrations of sorbitol increases the viscosity of the reaction, making unconventionally long extension times advantageous in certain embodiments of the methods of the invention; i.e., the use of extension times that are longer compared to extension times one of ordinary skill in the art would calculate for standard PCR reactions. Furthermore, as noted above for the annealing phase, sorbitol is a mild denaturant. Thus, in some embodiments of the methods of the invention, it may be advantageous to also use a lower temperature for extension than would be used by one of ordinary skill in the art for standard PCR reactions. Thus, for some embodiments, temperatures for extension are below the temperature reported for optimal activity of the polymerases used.

The number of cycles of PCR (denaturation, annealing and extension) used will determine the desired amount of amplification. PCR is an exponential amplification of DNA molecules. Thus, theoretically, after each cycle of PCR, there are twice the number of fragments that were present in the previous cycle. Typically, 20–30 cycles of PCR are performed. More typically, 25–30 cycles are performed, although cycle number is not particularly limited.

For some embodiments, it is advantageous to incubate the reactions at a certain temperature following the last phase of the last cycle of PCR. In some embodiments, a prolonged extension phase is selected. In other embodiments, an incubation at a low temperature (e.g., 4° C.) is selected.

In one embodiment of the invention, methods are provided for reducing stutter in the amplification of a microsatellite wherein a sample containing a microsatellite of interest is provided, wherein the microsatellite has a G+C content of greater than 50%. The sample is contacted with at least one enzyme having nucleic acid polymerase activity, and the sample is incubated with the enzyme for a sufficient amount of time and under conditions sufficient to amplify said microsatellite. The incubation is performed in the presence of an amount of sorbitol that is effective to reduce stutter relative to the amount of stutter observed in the absence of sorbitol. The PCR reaction includes primers that are selected to amplify the target microsatellite of interest and which are optionally tagged, dNTPs, buffer, the sample containing the template nucleic acid to be amplified, sorbitol and the polymerase.

In another embodiment of the invention, primer extension reactions may be performed with greater accuracy when conducted in the presence of sorbitol. In primer extension reactions, an oligonucleotide primer is permitted to bind to a specific target sequence on a nucleic acid molecule in the presence of dNTPs and a polymerase. The reaction is incubated and the polymerase polymerizes the dNTPs and extends the oligonucleotide primer in the 5' to 3' direction to form the complement of the target nucleic acid molecule. The primer may contain a detectable label, or the dNTPs used may contain a detectable label. Further, the dNTPs may be modified dNTPs, including, such as, but not limited to, dideoxynucleotide triphosphates.

The microsatellites amplified in the methods of the invention may be mononucleotide microsatellites, dinucleotide microsatellites, trinucleotide microsatellites, tetranucleotide microsatellites, and pentanucleotide microsatellites, and the microsatellites may include repeat motif interspersions. Mononucleotide microsatellites can be a repeat of C. The complementary strand of this portion of DNA would contain repeats of G. To denote the microsatellite with its complementary strand, the notation C/G is used. In some embodiments, the microsatellite is a dinucleotide microsatellite. Examples of dinucleotide microsatellites include, CG/CG. In other embodiments, the microsatellite is a trinucleotide microsatellite, including but not limited to CAG/CTG, CGA/TCG and CGG/CCG. In still other embodiments, the microsatellite is a tetranucleotide microsatellite, including, but not limited to TGCC/GGCA. Examples of loci that contain such tetranucleotide microsatellites include, but are not limited to D2S1338 (TGCC)(TTCC); and D7S809 (AGGA)(AGGC). In still other embodiments, the microsatellite is a pentanucleotide microsatellite, including, but not limited to CCCCT/AGGGG.

The microsatellites amplified in the method of the invention generally have a G+C content of greater than 50%. In some embodiments, the microsatellite has a G+C content of 66% or more. In other embodiments, the microsatellite has a G+C content of 75% or more. In other embodiments, the microsatellite has a G+C content of 100%.

The amount of sorbitol added to the PCR reaction is generally in an amount effective to reduce stutter relative to the amount of stutter observed in the absence of sorbitol. In some embodiments, the amount of sorbitol added is 1.5 to 3.5 M. In some embodiments, sorbitol is added in an amount of 2.0 to 3.0 M. In other embodiments, sorbitol is added in an amount of 2.0 M. The sorbitol may be added from a separate stock or may be added as part of another PCR reagent. For example, in one embodiment of the invention, the sorbitol is included in the DNA polymerase preparation and is added when the enzyme is added to the reaction. In another embodiment of the invention, the sorbitol is included with a preparation of magnesium ion containing reagent (e.g., $MgCl_2$ or $MgSO_4$) so that the sorbitol is added with the $MgCl_2$ or $MgSO_4$.

Sorbitol has chemical properties that may be exploited for various purposes. For example, sorbitol is rather hydrolytically inert, which may impart-a longer shelf-life to the PCR reagents. As another example, sorbitol possesses no acid-base properties, so it does not affect the pH of the PCR reaction when added in high concentrations.

In accordance with the embodiments of the methods of the invention, the addition of sorbitol to the reactions is effective in reducing stutter to between 90% and 20% of the amount of stutter obtained in the absence of sorbitol. In some embodiments, the amount of stutter observed with the addition of sorbitol is reduced to 90% or less than the amount observed in the absence of sorbitol. In some embodiments, the amount of stutter observed with the addition of sorbitol is reduced to 80% or less than the amount observed without the addition of sorbitol. In other embodiments, the amount of stutter observed with the addition of sorbitol is reduced to 70% or less than the amount observed without the addition of sorbitol. In other embodiments, the amount of stutter observed with the addition of sorbitol is reduced to 60% or less than the amount observed without the addition of sorbitol. In other embodiments, the amount of stutter observed with the addition of sorbitol is reduced to 50% or less than the amount observed without the addition of sorbitol. In other embodiments, the amount of stutter observed with the addition of sorbitol is reduced to 40% or less than the amount observed without the addition of sorbitol. In other embodiments, the amount of stutter observed with the addition of sorbitol is reduced to 30% or less than the amount observed without the addition of sorbitol. The reduction of stutter is measured by determining the percent stutter in the presence of sorbitol (+S), and in the absence of sorbitol (−S), and performing the following calculation (+S)/(−S)×100. Percent stutter is determined, for example, by the peak height of the stutter signal over the peak height of the allele signal times 100. Alternatively, percent stutter is determined by peak width at half peak height of the stutter signal over the peak width at half peak height of the allele signal times 100. In other embodiments, percent stutter is determined by area of the peak of the stutter signal over area of the peak of the allele signal times 100. Any other method of determining percent stutter in the presence of sorbitol relative to the percent stutter in the absence of sorbitol may be used, and the percent reduction determined.

In further embodiments of the invention, methods are provided in which a sample containing nucleic acid that is suspected of containing one or more microsatellites (e.g., mononucleotide microsatellites, dinucleotide microsatellites, trinucleotide microsatellites, and/or tetranucleotide microsatellites having a G+C content of greater than 50%) is contacted with an enzyme that polymerizes nucleotides in the presence of an effective amount of sorbitol to reduce observed stutter relative to the amount of stutter observed in the absence of sorbitol, and amplifying at least one nucleobase sequence containing at least one microsatellite of the nucleic acid contained in the sample.

In further embodiments of the invention, PCR reactions as described herein are employed to amplify fragments from at least one microsatellite region. In certain embodiments, the fragments are amplified with a detectable tag (e.g., a fluorophore-tagged primer) or with a hybridization enhancer (e.g., a minor groove binder). Where more than one microsatellite region is to be amplified, detectable tags are selected such that different products are easily distinguished. As an example, but not by way of limitation, different colored fluorophores may be used to amplify different microsatellites. Furthermore, the same color fluorophore may be used to amplify fragments containing microsatellites that generate fragments of different sizes which are readily discernable, e.g., by electrophoretic separation. The PCR products can be analyzed in on a sieving or non-sieving medium. In some embodiments of the invention, for example, the PCR products are analyzed by capillary electrophoresis as described in Wenz, H. et al. (1998) *Genome Res.* 8:69–80. In other embodiments of the invention, for example, the PCR products are analyzed by slab gel electrophoresis as described in Christensen, M. et al. (1999) *Scand. J. Clin. Lab. Invest.* 59(3): 167–177. Fragments may be analyzed by chromatography, e.g., size exclusion chromatography (SEC).

In certain embodiments, the methods of the invention decrease the number or intensity of stutter bands, or shadow bands, on standard gels. Thus, the methods of the invention provide for more simplified and more accurate interpretation of banding patterns on gels, with increased resolution of bands. Accordingly, for some embodiments of the invention, the PCR reactions may be analyzed on agarose or polyacrylamide gels using standard techniques.

In accordance with the embodiments of the invention, the use of sorbitol in the analysis of microsatellites by PCR provides a marked enhancement in the diagnostic capabilities of microsatellites in mono-, di-, tri-, tetra- and pentanucleotide repeat microsatellites.

In some embodiments, the invention provides kits. In some embodiments, the kits of the invention contain a concentrated stock solution of sorbitol for addition to the PCR reactions such that sorbitol is diluted to be present in an amount of 1.5 to 3.5 M in the PCR. Typically, the sorbitol is diluted to be present in an amount of 2 to 3 M. In addition to the sorbitol solution, the kits may contain at least one of the following reagents: dNTPs (either separately or as a mixture), DNA polymerase, buffer, and primers to amplify microsatellites. The kits may also contain conventional kit components, such as instructions for use.

Microsatellite markers that exhibit a high degree of polymorphism are exploited in many important applications. Recently, the A-repeat BAT loci have been used in studying microsatellite instability (MSI) which correlates with certain cancers (Chen et al. (1995) *Cancer Res.* 55:174–180; Ionov et al. (1993) *Nature* 363:558–561 De La Chapelle (1999) *Eur. J. Hum. Genet.* 7:407–408). However, due to the small allelic size differences in these markers and stutter during PCR, it has been difficult to determine whether the DNA samples are homozygous or heterozygous. Additionally, polymorphic variations at these loci in individuals of different ethnic origins supports the need to define the different allelic profiles and frequencies (Pyatt et al. (1999) *Am. J. Pathol.* 155:349–353).

Detection of genetic disorders associated with aberrant microsatellites is an application of the methods of the invention. Samples may be taken from tissues or individuals suspected of harboring aberrant microsatellites in their DNA and the DNA may be amplified by PCR in the presence of an sufficient amount of sorbitol under conditions sufficient to reduce stutter relative to observed stutter in the absence of sorbitol for microsatellites with a G+C content of greater than 50%. The resulting PCR products may be compared to PCR products from normal tissue, or tissue from normal individuals, and variation assessed. Aberrant microsatellites may indicate a propensity to develop a genetically-based disorder, or may indicate the presence of a genetically-based disease. Such disorders include, but are not limited to cancer, pre-cancerous conditions (e.g., chronic lymphocytic leukemia) and genetic disorders such as, but not limited to the spinocerebellar ataxias, Huntington disease, oculopharyngeal muscular dystrophy, myotonic dystrophy, and Fragile X Syndrome. As an example, but not by way of limitation, the fragile X syndrome may be diagnosed using the method of the invention by amplification, in the presence of a sufficient amount of sorbitol, the FRAXA locus, which has an unstable and pathogenic CGG/CCG trinucleotide repeat.

In a specific embodiment, PCR amplification reactions may be set up to amplify a trinucleotide repeat using the primers to amplify within the FRAXA locus. The sense primers of each of the loci may be tagged with a fluorophore. The PCR reactions may be set up as follows: 50 mM KCl, 10 mM Tris-HCl (pH=9.0), 0.1% Triton X-100, 4.5 mM $MgCl_2$, 1.0 mM each of dATP, dGTP, dCTP, and dTTP, 2.5 U Taq DNA polymerase and 2 M sorbitol. The reaction may then proceed as follows: 94° C. for 1 minutes, and 28 cycles of 94° C. for 15 seconds, 40° C. for 3 minutes and 65° C. for 5 minutes.

PCR reactions are then analyzed by denaturing samples and separating using a capillary gel electrophoresis protocol and using an ABI PRISM® 310 genetic analyzer, or by separating on a 4.5%, 29:1 acrylamide:bis acrylamide, 8 M urea gel prepared for an ABI 377 Automated Fluorescence DNA Sequencer. Fragment analysis may be analyzed with GeneScan Software from Applied Biosystems. Alteration in the size of the amplified fragment as compared to normal, control tissues or samples could be indicative of Fragile X Syndrome.

The methods of the invention are also useful in such applications as genetic mapping (linkage analysis). Linkage analysis may be accomplished, for example, by using a panel of primers to amplify a set of loci containing microsatellites that have a G+C content of greater than 50% in the presence of a sufficient amount of sorbitol to reduce the observation of stutter from that observed in the absence of sorbitol. Genetic loci such as D2S1338 and D7S809, for example, may be amplified for a given sample of DNA from an individual. The amplification may be done in the same reaction if the primers are differentially labeled (such as by using fluorophore tags) that will allow ready identification of PCR products following amplification.

In the field of human identity, tetranucleotide microsatellites are used in forensic casework, establishment of convicted felon databases, disaster and military victim identification (Fre'geau et al. (1993) *Biotechniques* 15:100–119). Furthermore, they have proved useful in forensics to identify human remains (Hagelberg et al. (1991) *Nature* 352:427–429; Hammond et al. (1994) *Am. J. Hum. Genet.* 55:175–189). In the analysis of museum specimens (Ellegren et al. (1991) *Nature* 354:113) and in parentage testing. Tetranucleotide microsatellites are specifically powerful in these applications, since multiple microsatellite tests that have matching probabilities of one in several billion individuals are now available. Examples of microsatellite containing alleles which can be used for paternity, forensic and other personal identification are D2S1338 (($TGCC)_n$ ($TTCC)_n$), and D7S809.

Also of special value in the identification of individuals is the PCR analysis of the highly polymorphic D loop of mitochondrial DNA, which contains a polymorphic C/G mononucleotide repeat; this analysis typically includes Sanger sequencing of the PCR product.

Personal identification tests may be performed on any specimen that contains nucleic acid such as bone, hair, blood, tissue and the like. DNA may be extracted from the specimen and a panel of primers to amplify a set of microsatellites used to amplify DNA in the presence of an effective amount of sorbitol to reduce stutter from the specimen to generate a set of amplified fragments. In forensic testing, the specimen's microsatellite amplification pattern is compared with a known sample the presumptive victim (the presumed matching source) or is compared to the pattern of amplified microsatellites derived from the presumptive victim's family members (e.g., the mother and father) wherein the same set of microsatellites is amplified in the presence of an effective amount of sorbitol to reduce stutter using the same primers. The pattern of microsatellite amplification may be used to confirm or rule out the identity of the victim. In paternity testing, the specimen is generally from the child and the comparison is made to the microsatellite pattern from the presumptive father, and may include matching with the microsatellite pattern from the child's mother. The pattern of microsatellite amplification may be used to confirm or rule out the identity of the father. The panel may include microsatellites with a G+C content of greater than 50% such as, for example, D2S1338 and D7S809. PCR conditions include 5–10 ng genomic DNA, 10 pmoles each fluorophore-tagged primer, 2.5 M sorbitol, 1 mM each dNTPs, 5 mM $MgCl_2$, 50 mM KCl, 10 mM Tris-HCl, 5 U DNA polymerase. PCR cycle conditions may be 1 min 94° C., followed by 30 cycles of 20 seconds at 94° C., 3 minutes at 50° C., 3 minutes at 60° C., followed by one cycle of 10 minutes at 60° C. The products are examined by capillary gel electrophoresis coupled with GeneScan 310 analysis.

Dinucleotide microsatellites are also used in paternity testing for cattle, dogs, horses and other animals (Primmer et al. (1995) *Mol. Ecol.* 4:493–498). In a clinical setting, microsatellite markers can be used to monitor the degree of donor engraftment in bone marrow transplants. In hospitals, microsatellite markers are useful in specimen matching tracking. More recently, microsatellite markers have also entered other fields of science such as population biology studies on human racial and ethnic group differences (Goldstein et al. (1995) *Proc. Natl. Acad. Sci. USA* 92:6723–6727) and on variation in animal and plant taxa (Bruford et al. (1993) *Curr. Biol.* 3:939–943).

Reduction in stutter bands in accordance with the present invention is useful in all of the above applications, which are illustrative and not limiting, because, inter alia, the interpretation of the data is facilitated by the method of the invention. The methods of the invention may be used in conjunction with the methods described in the references cited herein, the disclosure of each of which is incorporated herein by reference in its entirety. In particular, the methods of the invention will simplify analyses of forensic samples, and therefore find particular utility in the forensic field.

The invention will be further described using the following actual examples, which are merely illustrative of some embodiments of the invention. The examples should not be construed in any way to limit the scope of the invention, which is defined by the appended claims.

EXAMPLES

Example 1

PCR reactions were used to amplify the DNA tetranucleotide microsatellite, D2S1338 ((TGCC)(TTCC)) in the presence or absence of sorbitol (FIG. 1). The 50 ul reactions contained 20 mM Tris, 20 mM ammonium sulfate, 4.5 mM magnesium sulfate 1 mM each or dATP, dGTP, dCTP and dTTP, 12 pmoles oligonucleotide primers, 2 ng human genomic DNA template, 5U AmpliTaq Gold® DNA polymerase in water. In reactions in which sorbitol was added, the reactions contained 2.0 M sorbitol. The reaction conditions were as follows: 95° C. for 11 minutes, followed by 28 cycles of 94° C. for 30 seconds, 55° C. for 4 minutes and 69° C. for 6 minutes, followed by incubation at 60° C. for 45 minutes. Following PCR, samples were mixed with ROX fluorescent size marker (Applied Biosystems). Samples were denatured and separated using a protocol for capillary electrophoresis prepared for an ABI 310 Automated Genetic Analyzer according to the manufacturer's specifications. Fragment analysis data was analyzed with GeneScan Software from Applied Biosystems. For each set of peaks observed (see FIG. 1), each peak corresponds to a fluorescence labeled, single stranded DNA molecule. The position of the peak on the x axis corresponds to the length of the DNA molecule. The height of each peak corresponds to the relative amount of PCR product for this length, as determined by relative fluorescence intensity measured in arbitrary units. A stutter peak for the tetranucleotide repeat is found four peaks to the left of the main peak (where the "main peak" is the allele). A reduction in the height of the stutter peak relative to the main peak is indicative of a reduction in stutter. When measuring stutter reduction, the height of the stutter peak over the height of the main peak×100 provides the percent stutter. If there are multiple stutter peaks, they are not taken collectively. Rather the height of the main stutter peak over the height of the allele peak×100 gives the percent stutter. The results for the reactions with sorbitol, and control samples are shown in FIG. 1 and are summarized in Table 1:

TABLE 1

Results of sorbitol on amplification of tetranucleotide microsatellites
% Stutter

| Microsatellite | Control | + Sorbitol |
|---|---|---|
| Tetranucleotide | 8.3 | 5.1 (−39%) |

*percent stutter = Peak height of stutter signal/peak height of allele signal × 100; Percentage in parentheses is percent reduction of stutter of modified conditions over control.

The reference works, patents, patent applications, and scientific literature, and other printed publications, including accession numbers to GenBank database sequences, that are referred to herein are hereby incorporated by reference in their entirety.

As those skilled in the art will appreciate, numerous changes and modifications may be made to the embodiments of the invention without departing from the spirit of the invention. It is intended that all such variations fall within the scope of the invention.

What is claimed is:

1. A method for reducing stutter in the amplification of a polymorphic microsatellite comprising the steps of:
    (a) providing a sample comprising a microsatellite of interest, said microsatellite having a G+C content of greater than 50%;
    (b) contacting said sample with at least one enzyme having nucleic acid polymerase activity; and
    (c) incubating said sample with said enzyme for a time and under conditions sufficient to amplify said microsatellite;
   wherein said incubation is performed in the presence of an amount sorbitol effective to reduce said stutter relative to the amount of stutter observed in the absence of sorbitol.

2. A method for reducing stutter in the amplification of a polymorphic mononucleotide microsatellite comprising the steps of:
    (a) providing a sample comprising a microsatellite of interest, said microsatellite having a G+C content of greater than 50%;
    (b) contacting said sample with at least one enzyme having nucleic acid polymerase activity; and
    (c) incubating said sample with said enzyme for a time and under conditions sufficient to amplify said microsatellite;
   wherein said incubation is performed in the presence of an amount sorbitol effective to reduce said stutter relative to the amount of stutter observed in the absence of sorbitol.

3. The method of claim 2 wherein said stutter is reduced to 60% or less the amount of stutter obtained in the absence of sorbitol.

4. The method of claim 2 wherein said sorbitol is present in an amount of 1.5 to 3.5 M.

5. The method of claim 2 wherein said sorbitol is present in an amount of 2.0 to 3.0 M.

6. A method for reducing stutter in the amplification of a polymorphic dinucleotide microsatellite comprising the steps of:
    (a) providing a sample comprising a microsatellite of interest, said microsatellite having a G+C content of greater than 50%;

(b) contacting said sample with at least one enzyme having nucleic acid polymerase activity; and (c) incubating said sample with said enzyme for a time and under conditions sufficient to amplify said microsatellite;

wherein said incubation is performed in the presence of an amount of sorbitol effective to reduce said stutter relative to the amount of stutter observed in the absence of sorbitol.

7. The method of claim 6 wherein said stutter is reduced to 60% or less the amount of stutter obtained in the absence of sorbitol.

8. The method of claim 6 wherein said sorbitol is present in an amount of 1.5 to 3.5 M.

9. The method of claim 6 wherein said sorbitol is present in an amount of 2.0 to 3.0 M.

10. A method for reducing stutter in the amplification of a polymorphic trinucleotide microsatellite comprising the steps of:

(a) providing a sample comprising a microsatellite of interest, said microsatellite having a G+C content of greater than 50%;

(b) contacting said sample with at least one enzyme having nucleic acid polymerase activity; and (c) incubating said sample with said enzyme for a time and under conditions sufficient to amplify said microsatellite;

wherein said incubation is performed in the presence of an amount of sorbitol effective to reduce said stutter relative to the amount of stutter observed in the absence of sorbitol.

11. The method of claim 10 wherein said microsatellite comprises a repeat selected from the group consisting of CAG/CTG, CCG/CGG, and CGA/TCG.

12. The method of claim 10 wherein said microsatellite has a G+C content of 66% or more.

13. The method of claim 10 wherein said stutter is reduced to 60% or less the amount of stutter obtained in the absence of sorbitol.

14. The method of claim 10 wherein said sorbitol is present in an amount of 1.5 to 3.5 M.

15. The method of claim 10 wherein said sorbitol is present in an amount of 2.0 to 3.0 M.

16. A method for reducing stutter in the amplification of a polymorphic tetranucleotide microsatellite comprising the steps of:

(a) providing a sample comprising a microsatellite of interest, said microsatellite having a G+C content of greater than 50%;

(b) contacting said sample with at least one enzyme having nucleic acid polymerase activity; and (c) incubating said sample with said enzyme for a time and under conditions sufficient to amplify said microsatellite;

wherein said incubation is performed in the presence of an amount of sorbitol effective to reduce said stutter relative to the amount of stutter observed in the absence of sorbitol.

17. The method of claim 16 wherein said microsatellite comprises a TGCC/GGCA repeat.

18. The method of claim 16 wherein said microsatellite has a G+C content of 66% or more.

19. The method of claim 16 wherein said stutter is reduced to 60% or less the amount of stutter obtained in the absence of sorbitol.

20. The method of claim 16 wherein said sorbitol is present in an amount of 1.5 to 3.5 M.

21. The method of claim 16 wherein said sorbitol is present in an amount of 2.0 to 3.0 M.

22. A method for reducing stutter in the amplification of a polymorphic pentanucleotide microsatellite comprising the steps of:

(a) providing a sample comprising a microsatellite of interest, said microsatellite having a G+C content of greater than 50%;

(b) contacting said sample with at least one enzyme having nucleic acid polymerase activity; and (c) incubating said sample with said enzyme for a time and under conditions sufficient to amplify said microsatellite;

wherein said incubation is performed in the presence of an amount of sorbitol effective to reduce said stutter relative to the amount of stutter observed in the absence of sorbitol.

23. The method of claim 22 wherein said microsatellite comprises a CCCCT/AGGGG repeat.

24. The method of claim 22 wherein said microsatellite has a G+C content of 66% or more.

25. The method of claim 22 wherein said stutter is reduced to 60% or less the amount of stutter obtained in the absence of sorbitol.

26. The method of claim 22 wherein said sorbitol is present in an amount of 1.5 to 3.5 M.

27. The method of claim 22 wherein said sorbitol is present in an amount of 2.0 to 3.0 M.

28. The method of claim 1 wherein said microsatellite has a G+C content of 66% or more.

29. The method of claim 1 wherein said microsatellite has a G+C content of 75% or more.

30. The method of claim 1 wherein said microsatellite has a G+C content of 100%.

31. The method of claim 1 wherein said stutter is reduced to 90% or less than the amount of stutter obtained in the absence of sorbitol.

32. The method of claim 1 wherein said stutter is reduced to 80% or less than the amount of stutter obtained in the absence of sorbitol.

33. The method of claim 1 wherein said stutter is reduced to 70% or less than the amount of stutter obtained in the absence of sorbitol.

34. The method of claim 1 wherein said stutter is reduced to 60% or less the amount of stutter obtained in the absence of sorbitol.

35. The method of claim 1 wherein said stutter is reduced to 50% or less than the amount of stutter obtained in the absence of sorbitol.

36. The method of claim 1 wherein said stutter is reduced to 40% or less than the amount of stutter obtained in the absence of sorbitol.

37. The method of claim 1 wherein said stutter is reduced to 30% or less than the amount of stutter obtained in the absence of sorbitol.

38. The method of claim 1 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine, wherein each of said amounts of dNTP is least 0.5 mM.

39. The method of claim 1 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine, wherein each of said amounts of dNTP is least 1 mM.

40. The method of claim 1 wherein said sorbitol is present in an amount of 1.5 to 3.5 M.

41. The method of claim 1 wherein said sorbitol is present in an amount of 2.0 to 3.0 M.

42. A method comprising the steps of:
(a) providing a sample comprising a nucleic acid containing one or more polymorphic microsatellites selected from the group consisting of mononucleotide microsatellites, dinucleotide microsatellites, trinucleotide microsatellites, tetranucleotide microsatellites, and pentanucleotide microsatellites; and
(b) amplifying at least one nucleobase sequence of said nucleic acid, said nucleobase sequence comprising at least one of said microsatellites;
said amplified microsatellite having a G+C content of greater than 50%;
wherein said amplification is performed in the presence of sorbitol.

43. The method of claim 42 wherein the G+C content of at least one of said amplified microsatellites is 66% or more.

44. The method of claim 42 wherein the G+C content of at least one of said amplified microsatellites is 75% or more.

45. The method of claim 42 wherein the G+C content of at least one of said amplified microsatellites is 100%.

46. The method of claim 42 wherein said amplification comprises contacting said nucleobase sequence with an enzyme having a polymerase activity.

47. The method of claim 46 wherein the enzyme having polymerase activity is selected from the group consisting of AmpliTaq Gold® DNA polymerase; AmpliTaq® DNA Polymerase; AmpliTaq® DNA Polymerase, Stoffel fragment; rTth DNA Polymerase; rTth DNA Polymerase XL; Tne, Bst DNA polymerase large fragment from *Bacillus stearothermophilus;* Vent and Vent Exo- from *Thermococcus lioralis;* Tma from *Thermotoga maritima;* Deep Vent and Deep Vent Exo- and Pfu from Pyrococcus; and mutants, variants and derivatives thereof.

48. The method of claim 42 wherein said amplified microsatellite is a mononucleotide microsatellite.

49. The method of claim 42 wherein said amplified microsatellite is a dinucleotide microsatellite.

50. The method of claim 42 wherein said amplified microsatellite is a trinucleotide microsatellite.

51. The method of claim 42 wherein said amplified microsatellite is a tetranucleotide microsatellite.

52. The method of claim 42 wherein said amplified microsatellite is a pentanucleotide microsatellite.

53. The method of claim 42 wherein said incubation is performed in the presence of a set of dNTPs, said set comprising an amount of dNTP complementary to adenosine, an amount of dNTP complementary to guanosine, an amount of dNTP complemnentary to cytidine and an amount of dNTP complementary to thymine, wherein each of said amounts of dNTP is least 0.5 mM.

54. The method of claim 42 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine, wherein each of said amounts of dNTP is least 1 mM.

55. The method of claim 42 wherein said sorbitol is present in an amount of 1.5 to 3.5 M.

56. The method of claim 42 wherein said sorbitol is present in an amount of 2.0 to 3.0 M.

57. A method comprising the steps of:
(a) providing a sample comprising a nucleic acid that contains one or more polymorphic microsatellites selected from the group consisting of mononucleotide microsatellites, dinucleotide microsatellites, trinucleotide microsatellites, tetranucleotide microsatellites, and pentanucleotide microsatellites; and
(b) amplifying at least one nucleobase sequence of said nucleic acid, said nucleobase sequence comprising at least one of said microsatellites; said amplified microsatellite having a G+C content of greater than 50%;
wherein said amplification is performed in the presence of sorbitol in an amount of 1.5 to 3.5 M, and in the presence of a set of dNTPs, said set comprising an amount of dNTP complementary to adenosine, an amount of dNTP complementary to guanosine, an amount of dNTP complementary to cytidine and an amount of dNTP complementary to thymine, wherein each of said amounts of dNTP is least 0.5 mM.

58. A method for performing polymerase chain reaction amplification of a polymorphic microsatellite selected from the group consisting of mononucleotide microsatellites, dinucleotide microsatellites, trinucleotide microsatellites, tetranucleotide microsatellites and pentanucleotide microsatellites, said amplified microsatellite having a G+C content of greater than 50%, said method comprising the step of contacting said microsatellite with a polymerase in the presence of an amount of sorbitol effective to reduce the amount of stutter arising from said amplification, relative to the amount of such stutter observed in the absence of sorbitol.

59. The method of claim 58 wherein said polymerase is selected from the group consisting of AmpliTaq Gold® DNA polymerase; AmpliTaq® DNA Polymerase; AmpliTaq® DNA Polymerase, Stoffel fragment; rTth DNA Polymerase; rTth DNA Polymerase XL; Tne, Bst DNA polymerase large fragment from *Bacillus stearothermophilus;* Vent and Vent Exo- from *Thermococcus litoralis;* Tma from *Thermotoga maritima;* Deep Vent and Deep Vent Exo- and Pfu from Pyrococcus; and mutants, variants and derivatives thereof.

60. The method of claim 58 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine, wherein each of said amounts of dNTP is least 0.5 mM.

61. The method of claim 58 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine, wherein each of said amounts of dNTP is least 1 mM.

62. The method of claim 58 wherein said sorbitol is present in an amount of 1.5 to 3.5 M.

63. The method of claim 58 wherein said sorbitol is present in an amount of 2.0 to 3.0 M.

64. A method of gene typing comprising amplifying a plurality of regions of DNA from a sample containing DNA from a subject, wherein said regions comprise at least one polymorphic microsatellite selected from the group consisting of a mononucleotide repeat, a dinucleotide repeat, a trinucleotide repeat, a tetranucleotide repeat, and a pentanucleotide repeat, said microsatellite having a G+C content of greater than 50%, wherein said amplification comprises the steps of:
(a) contacting said DNA with a enzyme at least one enzyme having nucleic acid polymerase activity;
(b) incubating said sample with said enzyme for a time and under conditions sufficient to amplify said regions; and (c) separating amplified regions, forming a microsatellite pattern;

wherein said incubation is performed in the presence of an amount of sorbitol effective to reduce said stutter relative to the amount of stutter observed in the absence of sorbitol.

65. The method of claim 64 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine; wherein each of said amounts of dNTP is least 0.5 mM.

66. The method of claim 64 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine; wherein each of said amounts of dNTP is least 1 mM.

67. The method of claim 64 wherein said sorbitol is present in an amount of 1.5 to 3.5 M.

68. The method of claim 64 wherein said sorbitol is present in an amount of 2.0 to 3.0 M.

69. A method of personal genetic identification comprising amplifying a plurality of regions of DNA from a sample containing DNA from a subject, wherein said regions comprise at least one polymorphic microsatellite selected from the group consisting of a mononucleotide repeat, a dinucleotide repeat, a trinucleotide repeat, a tetranucleotide repeat, and a pentanucleotide repeat, wherein said microsatellite has a G+C content of greater than 50%, wherein said amplification comprises the steps of:

(a) contacting said DNA with a enzyme at least one enzyme having nucleic acid polymerase activity; and (b) incubating said sample with said enzyme for a time and under conditions sufficient to amplify said regions;

(c) separating amplified regions, forming a microsatellite pattern; and (d) comparing said microsatellite pattern with a corresponding microsatellite pattern derived from the a DNA sample from a second source;

wherein said incubation is performed in the presence of an amount of an sorbitol effective to reduce said stutter relative to the amount of stutter observed in the absence of sorbitol.

70. The method of claim 69 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine; wherein each of said amounts of dNTP is least 0.5 mM.

71. The method of claim 69 wherein said incubation is performed in the presence of a set of dNTPs, said set comprising an amount of dNTP complementary to adenosine, an amount of dNTP complementary to guanosine, an amount of dNTP complementary to cytidine and an amount of dNTP complementary to thymine; wherein each of said amounts of dNTP is least 1 mM.

72. The method of claim 69 wherein said sorbitol is present in an amount of 1.5 to 3.5 M.

73. The method of claim 69 wherein said sorbitol is present in an amount of 2.0 to 3.0 M.

74. The method according to any of claims 1, 2, 6, 10, 16, 22, 42, 57, 58, 64 or 69 wherein said amplification is achieved by the polymerase chain reaction.

75. The method according to any of claims 1, 2, 6, 10, 16, 22, 42, 57, 58, 64 or 69 wherein said sample is of eukaryotic origin.

76. The method of claim 75 wherein the eukaryote is of mammalian origin.

77. The method of claim 76 wherein the mammal is of human origin.

* * * * *